US009931392B2

(12) United States Patent
Wren et al.

(10) Patent No.: US 9,931,392 B2
(45) Date of Patent: Apr. 3, 2018

(54) GLYCOSYLATION METHOD

(71) Applicant: London School of Hygiene and Tropical Medicine, London (GB)

(72) Inventors: Brendan Wren, London (GB); Jon Cuccui, London (GB); Sherif Abouelhadid, London (GB)

(73) Assignee: London School of Hygiene and Tropical Medicine, London (GB)

(*) Notice: Subject to any disclaimer, the term of this patent is extended or adjusted under 35 U.S.C. 154(b) by 6 days.

(21) Appl. No.: 14/655,128

(22) PCT Filed: Jan. 17, 2014

(86) PCT No.: PCT/GB2014/050133
§ 371 (c)(1),
(2) Date: Jun. 24, 2015

(87) PCT Pub. No.: WO2014/111724
PCT Pub. Date: Jul. 24, 2014

(65) Prior Publication Data

US 2015/0344928 A1 Dec. 3, 2015

(30) Foreign Application Priority Data

Jan. 18, 2013 (GB) .................................. 1300956.8
Jan. 21, 2013 (GB) .................................. 1301023.6
May 20, 2013 (GB) .................................. 1309068.3

(51) Int. Cl.
*C12N 9/10* (2006.01)
*C12P 21/00* (2006.01)
(Continued)

(52) U.S. Cl.
CPC .......... *A61K 39/105* (2013.01); *A61K 39/092* (2013.01); *C12N 1/20* (2013.01);
(Continued)

(58) Field of Classification Search
None
See application file for complete search history.

(56) References Cited

U.S. PATENT DOCUMENTS

2003/0013175 A1 1/2003 Koizumi et al.
2010/0062484 A1 3/2010 Aebi
(Continued)

FOREIGN PATENT DOCUMENTS

JP 2005-046031 A 2/2005
WO WO 1999/54342 A1 10/1999
(Continued)

OTHER PUBLICATIONS

Guo et al., "Protein tolerance to random amino acid change", Proceedings of the National Academy of Sciences USA, vol. 101, No. 25, pp. 9205-9210, 2004.*
(Continued)

*Primary Examiner* — Richard C Ekstrom
(74) *Attorney, Agent, or Firm* — Klarquist Sparkman, LLP

(57) ABSTRACT

The invention relates to microbial host cells engineered to produce glycoconjugate vaccines by stable integration of an acceptor protein and an oligosaccharyltransferase into the host's genome, wherein expression of the oligosaccharyltransferase is regulated.

27 Claims, 6 Drawing Sheets

(51) Int. Cl.
*A61K 39/02* (2006.01)
*C12N 15/70* (2006.01)
*C12N 15/74* (2006.01)
*C12N 1/20* (2006.01)
*A61K 39/09* (2006.01)

(52) U.S. Cl.
CPC ........... *C12N 9/1048* (2013.01); *C12N 15/70* (2013.01); *C12N 15/74* (2013.01); *C12P 21/005* (2013.01)

(56) References Cited

U.S. PATENT DOCUMENTS

2010/0137565 A1 6/2010 Javaud et al.
2011/0274720 A1 11/2011 Wacker et al.
2015/0344928 A1* 12/2015 Wren .................... C12P 21/005 530/395

FOREIGN PATENT DOCUMENTS

WO WO 2003/102191 A1 12/2003
WO WO 2007/035897 A2 3/2007
WO WO 2008/021076 A2 2/2008
WO WO 2008/133645 A2 11/2008
WO WO 2009/026131 A2 2/2009
WO WO 2009026131 A2 * 2/2009 ............. C12N 15/70
WO WO 2009/104074 A2 8/2009
WO WO 2009104074 A2 * 8/2009 ......... A61K 39/0258
WO WO 2011027116 A1 * 3/2011 ........... C12N 9/1051
WO WO 2011/115483 A1 9/2011
WO WO 2011/138361 A1 11/2011
WO WO 2012/158701 A1 11/2012

OTHER PUBLICATIONS

Feldman et al., "Engineering N-linked Protein Glycosylation with Diverse O Antigen Lipopolysaccharide Structures in *Escherichia coli,*" *Proc Natl Acad Sci. USA* 102:3016-3021, 2005.

Prior et al., "Characterization of the O Antigen Gene Cluster and Structural Analysis of the O Antigen of *Francisella tularensis* subsp. *tularensis,*" *J Med Microbiol.* 52:845-851, 2003.

Conlan et al., "Mice Vaccinated with the *O*-antigen of *Francisella tularensis* LVS Lipopolysaccharide Conjugated to Vovine Serum Albumin Develop Varying Degrees of Protective Immunity Against Systemic or Aerosol Challenge with Virulent type A and Type B Strains of the Pathogen," *Vaccine* 20:3465-3471, 2002.

Cuccui et al., "Exploitation of Bacterial *N*-linked Glycosylation to Develop a Novel Recombinant Glycoconjugate Vaccine Against *Francisella tularensis*," *Open Biol.* 3:130002, 2013.

Dagan et al., "Glycoconjugate Vaccines and Immune Interference: A Review," *Vaccine* 28:5513-5523, 2010.

Feldman et al., "Engineering N-linked Protein Glycosylation with Diverse O Antigen Lipopolysaccharide Structures in *Escherichia coli*," *Proc Nati Acad Sci. USA* 02:3016-3021, 2005.

Great Britain Search Report dated Jul. 16, 2013 for Great Britain Application No. GB1301085.5.

Great Britain Search Report dated Jul. 18, 2013 for Great Britain Application No. GB1300956.8.

Ihssen et al., "Production of Glycoprotein Vaccines in *Escherichia coli*," *Microbiol. Cell Factories* 9:61, 2010.

Kim et al., "Genetic Modification of the O-Polysaccharide of *Francisella tularensis* Results in an Avirulent Live Attenuated Vaccine," *J Infect Dis.* 205:1056-1065, 2012.

Kowarik et al., "N-Linked Glycosylation of Folded Proteins by the Bacterial Oligosaccharyltransferase," *Science* 314:1148-1150, 2006.

Nikel and Lorenzo, "Implantation of Unmarked Regulatory and Metabolic Modules in Gram-Negative Bacteria with Specialised Mini-Transposon Delivery Vectors," *J Biotechnol.* 163:143-154, 2013.

Prior et al., "Characterization of the O Antigen Gene Cluster and Structural Analysis of the O Antigen of *Francisella tularensis* subsp. *tularensis*," *J Med Microbial.* 52:845-851, 2003.

Sabido et al., "A Novel Plasmid Vector Designed for Chromosomal Gene Integration and Expression: Use for Developing a Genetically Stable *Escherichia coli* Melanin Production Strain," *Plasmid* 69:16-23, 2013.

Terra et al., "Recent Developments in Bacterial Protein Glycan Coupling Technology and Glycoconjugate Vaccine Design," *J Med Microbiol.* 61:919-926, 2012.

* cited by examiner

Figure 3A:
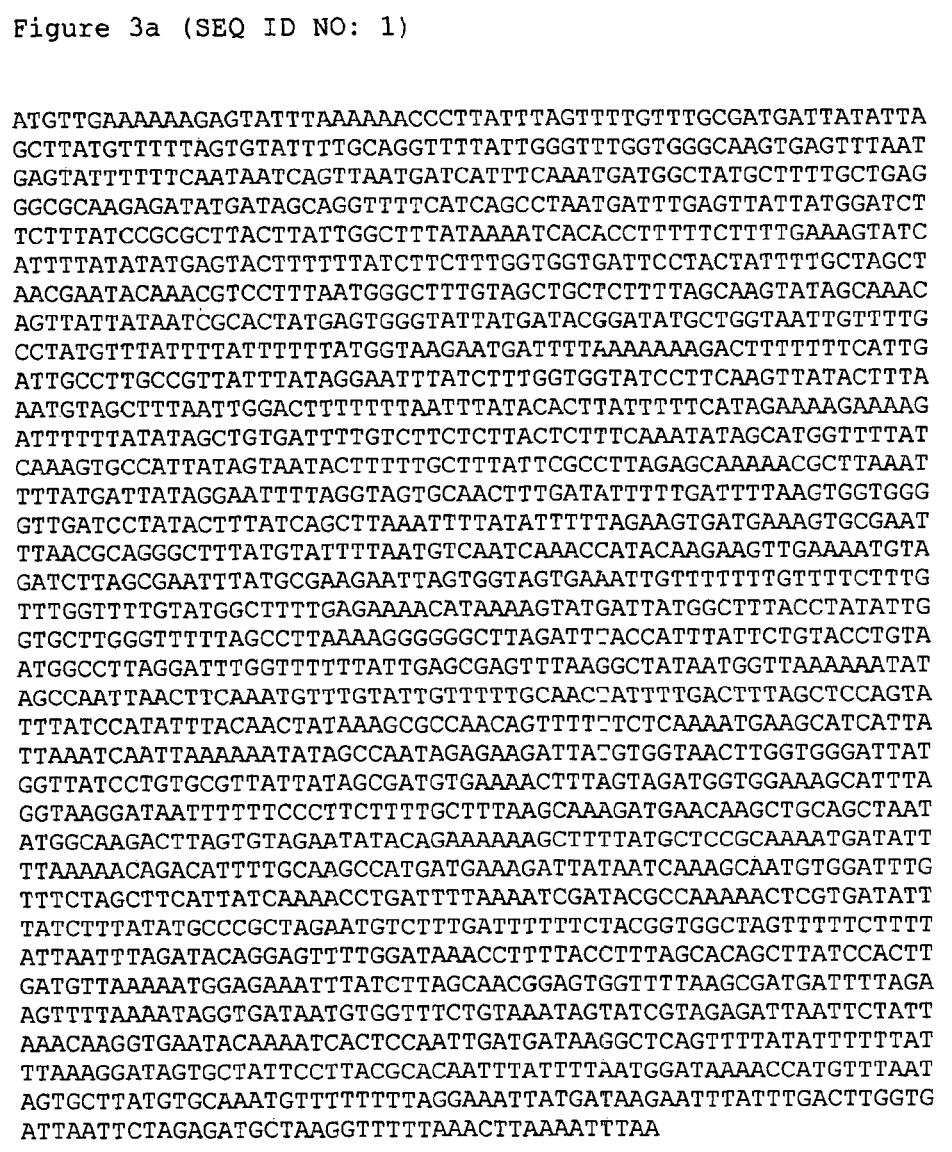

Figure 3a (SEQ ID NO: 1)

ATGTTGAAAAAAGAGTATTTAAAAAACCCTTATTTAGTTTTGTTTGCGATGATTATATTA
GCTTATGTTTTTAGTGTATTTTGCAGGTTTTATTGGGTTTGGTGGGCAAGTGAGTTTAAT
GAGTATTTTTTCAATAATCAGTTAATGATCATTTCAAATGATGGCTATGCTTTTGCTGAG
GGCGCAAGAGATATGATAGCAGGTTTTCATCAGCCTAATGATTTGAGTTATTATGGATCT
TCTTTATCCGCGCTTACTTATTGGCTTTATAAAATCACACCTTTTTCTTTTGAAAGTATC
ATTTTATATATGAGTACTTTTTTATCTTCTTTGGTGGTGATTCCTACTATTTTGCTAGCT
AACGAATACAAACGTCCTTTAATGGGCTTTGTAGCTGCTCTTTTAGCAAGTATAGCAAAC
AGTTATTATAATCGCACTATGAGTGGGTATTATGATACGGATATGCTGGTAATTGTTTTG
CCTATGTTTATTTTATTTTTTATGGTAAGAATGATTTTAAAAAAAGACTTTTTTTCATTG
ATTGCCTTGCCGTTATTTATAGGAATTTATCTTTGGTGGTATCCTTCAAGTTATACTTTA
AATGTAGCTTTAATTGGACTTTTTTTAATTTATACACTTATTTTTCATAGAAAAGAAAAG
ATTTTTTATATAGCTGTGATTTTGTCTTCTCTTACTCTTTCAAATATAGCATGGTTTTAT
CAAAGTGCCATTATAGTAATACTTTTTGCTTTATTCGCCTTAGAGCAAAAACGCTTAAAT
TTTATGATTATAGGAATTTTAGGTAGTGCAACTTTGATATTTTTGATTTTAAGTGGTGGG
GTTGATCCTATACTTTATCAGCTTAAATTTTATATTTTTAGAAGTGATGAAAGTGCGAAT
TTAACGCAGGGCTTTATGTATTTTAATGTCAATCAAACCATACAAGAAGTTGAAAATGTA
GATCTTAGCGAATTTATGCGAAGAATTAGTGGTAGTGAAATTGTTTTTTTGTTTTCTTTG
TTTGGTTTTGTATGGCTTTTGAGAAAACATAAAAGTATGATTATGGCTTTACCTATATTG
GTGCTTGGGTTTTTAGCCTTAAAAGGGGGGCTTAGATTTACCATTTATTCTGTACCTGTA
ATGGCCTTAGGATTTGGTTTTTTATTGAGCGAGTTTAAGGCTATAATGGTTAAAAAATAT
AGCCAATTAACTTCAAATGTTTGTATTGTTTTTGCAACTATTTTGACTTTAGCTCCAGTA
TTTATCCATATTTACAACTATAAAGCGCCAACAGTTTTTTCTCAAAATGAAGCATCATTA
TTAAATCAATTAAAAAATATAGCCAATAGAGAAGATTATGTGGTAACTTGGTGGGATTAT
GGTTATCCTGTGCGTTATTATAGCGATGTGAAAACTTTAGTAGATGGTGGAAAGCATTTA
GGTAAGGATAATTTTTTCCCTTCTTTTGCTTTAAGCAAAGATGAACAAGCTGCAGCTAAT
ATGGCAAGACTTAGTGTAGAATATACAGAAAAAAGCTTTTATGCTCCGCAAAATGATATT
TTAAAAACAGACATTTTGCAAGCCATGATGAAAGATTATAATCAAAGCAATGTGGATTTG
TTTCTAGCTTCATTATCAAAACCTGATTTTAAAATCGATACGCCAAAAACTCGTGATATT
TATCTTTATATGCCCGCTAGAATGTCTTTGATTTTTTCTACGGTGGCTAGTTTTTCTTTT
ATTAATTTAGATACAGGAGTTTTGGATAAACCTTTTACCTTTAGCACAGCTTATCCACTT
GATGTTAAAAATGGAGAAATTTATCTTAGCAACGGAGTGGTTTTAAGCGATGATTTTAGA
AGTTTTAAAATAGGTGATAATGTGGTTTCTGTAAATAGTATCGTAGAGATTAATTCTATT
AAACAAGGTGAATACAAAATCACTCCAATTGATGATAAGGCTCAGTTTTATATTTTTTAT
TTAAAGGATAGTGCTATTCCTTACGCACAATTTATTTTAATGGATAAAACCATGTTTAAT
AGTGCTTATGTGCAAATGTTTTTTTTAGGAAATTATGATAAGAATTTATTTGACTTGGTG
ATTAATTCTAGAGATGCTAAGGTTTTTAAACTTAAAATTTAA

Figure 3b (SEQ ID 2)

MLKKEYLKNPYLVLFAMIILAYVFSVFCRFYWVWWASEFNEYFFNNQLMIISNDGYAFAEGARDMIAGFHQPNDL
SYYGSSLSALTYWLYKITPFSFESIILYMSTFLSSLVVIPTILLANEYKRPLMGFVAALLASIANSYYNRTMSGY
YDTDMLVIVLPMFILFFMVRMILKKDFFSLIALPLFIGIYLWWYPSSYTLNVALIGLFLIYTLIFHRKEKIFYIA
VILSSLTLSNIAWFYQSAIIVILFALFALEQKRLNFMIIGILGSATLIFLILSGGVDPILYQLKFYIFRSDESAN
LTQGFMYFNVNQTIQEVENVDLSEFMRRISGSEIVFLFSLFGFVWLLRKHKSMIMALPILVLGFLALKGGLRFTI
YSVPVMALGFGFLLSEFKAIMVKKYSQLTSNVCIVFATILTLAPVFIHIYNYKAPTVFSQNEASLLNQLKNIANR
EDYVVTWWDYGYPVRYYSDVKTLVDGGKHLGKDNFFPSFALSKDEQAAANMARLSVEYTEKSFYAPQNDILKTDI
LQAMMKDYNQSNVDLFLASLSKPDFKIDTPKTRDIYLYMPARMSLIFSTVASFSFINLDTGVLDKPFTFSTAYPL
DVKNGEIYLSNGVVLSDDFRSFKIGDNVVSVNSIVEINSIKQGEYKITPIDDKAQFYIFYLKDSAIPYAQFILMD
KTMFNSAYVQMFFLGNYDKNLFDLVINSRDAKVFKLKI

Figure 4 (SEQ ID 13)

5'ATGTCCAATTTACTGACCGTACACCAAAATTTGCCTGCATTACCGGTCGATGCAACGAGTGATGAGGTTCGCA
AGAACCTGATGGACATGTTCAGGGATCGCCAGGCGTTTTCTGAGCATACCTGGAAAATGCTTCTGTCCGTTTGCC
GGTCGTGGGCGGCATGGTGCAAGTTGAATAACCGGAAATGGTTTCCCGCAGAACCTGAAGATGTTCGCGATTATC
TTCTATATCTTCAGGCGCGCGGTCTGGCAGTAAAAACTATCCAGCAACATTTGGGCCAGCTAAACATGCTTCATC
GTCGGTCCGGGCTGCCACGACCAAGTGACAGCAATGCTGTTTCACTGGTTATGCGGCGGATCCGAAAAGAAAACG
TTGATGCCGGTGAACGTGCAAAACAGGCTCTAGCGTTCGAACGCACTGATTTCGACCAGGTTCGTTCACTCATGG
AAAATAGCGATCGCTGCCAGGATATACGTAATCTGGCATTTCTGGGGATTGCTTATAACACCCTGTTACGTATAG
CCGAAATTGCCAGGATCAGGGTTAAAGATATCTCACGTACTGACGGTGGGAGAATGTTAATCCATATTGGCAGAA
CGAAAACGCTGGTTAGCACCGCAGGTGTAGAGAAGGCACTTAGCCTGGGGGTAACTAAACTGGTCGAGCGATGGA
TTTCCGTCTCTGGTGTAGCTGATGATCCGAATAACTACCTGTTTTGCCGGGTCAGAAAAAATGGTGTTGCCGCGC
CATCTGCCACCAGCCAGCTATCAACTCGCGCCCTGGAAGGGATTTTTGAAGCAACTCATCGATTGATTTACGGCG
CTAAGGATGACTCTGGTCAGAGATACCTGGCCTGGTCTGGACACAGTGCCCGTGTCGGAGCCGCGCGAGATATGG
CCCGCGCTGGAGTTTCAATACCGGAGATCATGCAAGCTGGTGGCTGGACCAATGTAAATATTGTCATGAACTATA
TCCGTAACCTGGATAGTGAAACAGGGGCAATGGTGCGCCTGCTGGAAGATGGCGATTAG-3'

Figure 5 (SEQ ID 14)

5'ATGAGCCAGTTCGATATCCTGTGTAAAACCCCGCCTAAGGTGCTTGTTCGTCAGTTTGTGGAAAGGTTTGAAA
GACCTTCAGGTGAGAAAATAGCATCCTGTGCTGCTGAACTAACCTATTTATGTTGGATGATTACACATAACGGAA
CAGCAATCAAGAGAGCCACATTCATGAGCTATAATACTATCATAAGCAATTCGCTGAGTTTCGATATTGTCAATA
AATCACTCCAGTTTAAATACAAGACGCAAAAAGCAACAATTCTGGAAGCCTCATTAAAGAAATTGATTCCTGCTT
GGGAATTTACAATTATTCCTTACAACGGACAAAAACATCAATCTGATATCACTGATATTGTAAGTAGTTTGCAAT
TACAGTTCGAATCATCGGAAGAAGCAGATAAGGGAAATAGCCACAGTAAAAAAATGCTTAAAGCACTTCTAAGTG
AGGGTGAAAGCATCTGGGAGATCACTGAGAAAATACTAAATTCGTTTGAGTATACTTCGAGATTTACAAAAACAA
AAACTTTATACCAATTCCTCTTCCTAGCTACTTTCATCAATTGTGGAAGATTCAGCGATATTAAGAACGTTGATC
CGAAATCATTTAAATTAGTCCAAAATAAGTATCTGGGAGTAATAATCCAGTGTTTAGTGACAGAGACAAAGACAA
GCGTTAGTAGGCACATATACTTCTTTAGCGCAAGGGGTAGGATCGATCCACTTGTATATTTGGATGAATTTTTGA
GGAATTCTGAACCAGTCCTAAAACGAGTAAATAGGACCGGCAATTCTTCAAGCAATAAACAGGAATACCAATTAT
TAAAAGATAACTTAGTCAGATCGTACAATAAAGCTTTGAAGAAAAATGCGCCTTATCCGATCTTTGCTATAAAAA
ATGGCCCAAAATCTCACATTGGAAGACATTTGATGACCTCATTTCTTTCAATGAAGGGCCTAACGGAGTTGACTA
ATGTTGTGGGAAATTGGAGCGATAAGCGTGCTTCTGCCCGTGGCCAGGACAACGTATACTCATCAGATAACAGCAA
TACCTGATCACTACTTCGCACTAGTTTCTCGGTACTATGCATATGATCCAATATCAAAGGAAATGATAGCATTGA
AGGATGAGACTAATCCAATTGAGGAGTGGCAGCATATAGAACAGCTAAAGGGTAGTGCTGAAGGAAGCATACGAT
ACCCCGCATGGAATGGGATAATATCACAGGAGGTACTAGACTACCTTTCATCCTACATAAATAGACGCATATAG-
3'

Figure 8

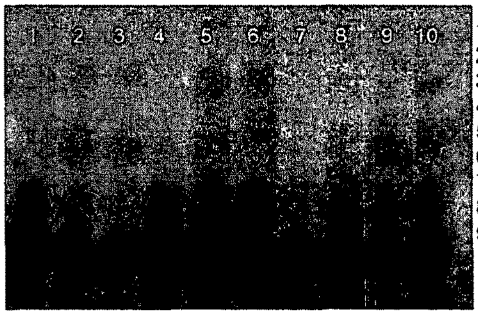

1: *App* WT+CjH+peptide
2: *App* PglB+Cj+peptide (1:1)
3: *E. coli* pglB+CjH+peptide (1:1)
4: Peptide only
5: *App* WT+peptide
6: *App* PglB+peptide
7: *E. coli* PglB+peptide
8: Glycan + peptide
9: *App* PglB+CjH+peptide (1:4)
10: *App* WT+CjH+peptide (1:4)

Figure 9 (SEQ ID 22) Campylobacter sputorum

ATGTCAAATTTTAATTTCGCTAAATTTCTAAATAAATTACCTAGACTTTCTAAACATACTATTTTAAT
GATTGTTTTAGCTGTTTGTTTTGGGATATTTTGCAGATTTTACTGGGTAGTTTGGGCTAGTGCTTATC
CGCATTTTATATGGAATGATCAGCTTATGATAAGCACAAATGACGGATATGCATTTGCTGAGGGCACA
AGAGATATGATAGCTGGTTTTCATCAACCAAACGATCTTTCTTACTATGGCTCATCTCTTTCGACGCT
TAGCATGTGGTTATATAACATTTTGCCATTTTCATTAGAAACTATACTTTTGTATATGAGTACATTTT
TATCTCCACTCTTAGCTGTGCCTTTGATACTTATAGGTAAAGAACTAAACGCTTCAAAAGCGGGTTTT
ATAGCTGCACTTCTAGCTATTATTGCAAATAGTTATTATAATAGAACAATGAGTGGATATTACGATAC
GGATATGCTAAATATCACTCTTCCTATGATGGTTTTTTGGAGCATAACAAGACTTGTTCAAAGAAAAG
AGAGAGTAAATTTAATATTTATTCCGGTTTTTATGGCGATATATGGATGGTGGTATCCATCTTCTTAC
TCACTATTACTTGCCATGATTGGAATGTTTTTTTTATATACCATTGTTTTTGAAAGATACGAAAAACT
AAACTATGAAGCTATGGTTTTTATGATTTTAGCAATCACAAGCTTTTCTATACAAATTAAATTTATTA
TAGTTATTGTTTTGTATGCTTTAATCTATTTTTACCAAAGATTTTTTGATAAAAAAGTAATATTTGCA
TTAATTATGGCTTCGTTAATATGCTTTATATGGCTTGGCGGGCTAAACCCTATACTTTTTAACATTAA
ATTTTATATATTTAGAGACATTGCAGATAGCGGTGATGCTGTTTTTAAATTTTTCAATGTAAATCAAA
CAATAAGAGAAAGTTCTGCGATAGATTTTAACACAGTTGTAACTAGGATTAGCGGGCATTTAATAGTA
TTTTTGGTATCTATTATAGGATATATTTTATTTATAAAAAACAATAAAATTTTACTACTAACTTTACC
GATTCTGTTTTTGGGTCTTATGTCATTTAAAAGTGGTTTAAGATTTACAATATACTCAGTTCCAGTAA
TGGCTCTTGGTTTTGGCTATTTTGTTATGTATTGTTTTGCAAAAATAGATATAAAAGATCGTTTTTTA
GGTTATGTGTTTTTATTTGTTGTAACATTTAGTGCATTATATCCATCTTTAAAACATATTTATGATTA
TAAAGTATTTCCTGTTTTTACACATAGCGAAGTTGAAAGTTTGGATAATTTAAAAAATATTGCAAAAA
GAGAAGATTATGTGCTTTCTTGGTGGGATTATGGTTATCCGATCAGATATTATTCAGATGTAAAAACT
CTCATAGATGGAGGAAAACATCTTGGAAGTGATAACTTCGCCGTTAGCTTTGCACTTGGAAGCGATCA
AAATAGCTCTGCAAATATGGCAAGATTAGAAGTTGAATATACAGAAAAAAATTATGAAGAAAAATTTG
GATTAAATTTAAAAAAGATGATGAAAGATTATAATGCTACAAATGTTAATGAGTTTTTATTATCATTA
AAAGATGAAAATTTAACTCTGCCAAAGCAAACAAGAGATATTTATTACTATTTACCAGATAGAATGAT
ATACATATATCCGATAGTGCTAGATTTTTCTAGACTTGATTTGACAACAGGGCAAGAATTTGCCCAGC
CGTTTTTTATGGTTAGTGAGAGATTTTCAGCTACAAATGATAATCAAATAATGTTAAATAACAATGTC
ATATTAAGTAATGATGGCACTAAATTATCGATAAATGGCAACTCTTATAGTGTAAATACATATGTTGA
AACAAGTTATGATCAAAACGAAAAAATTAAATGTAAATTATTTTAACATAGATCCAAATAGCAATTTTT
ATGTGATTTTTATGAAAGATTATTTGAGAATTTTGGTTTTAGATAAAACTTTGTATGATAGTGCGTAT
ATTCAACTTTTTGTATTAGAAAATTATGATAAAAATTTATTTGAACCAGTGATTTTAAACGGATCAAC
TAAAATTTATAAACTCAAAAAATGA

Figure 10 (SEQ ID NO: 23)

MSNFNFAKFLNKLPRLSKHTILMIVLAVCFGIFCRFYWVVWASAYPHFIWNDQLMISTNDGYAFAEGT
RDMIAGFHQPNDLSYYGSSLSTLSMWLYNILPFSLETILLYMSTFLSPLLAVPLILIGKELNASKAGF
IAALLAIIANSYYNRTMSGYYDTDMLNITLPMMVFWSITRLVQRKERVNLIFIPVFMAIYGWWYPSSY
SLLLAMIGMFFLYTIVFERYEKLNYEAMVFMILAITSFSIQIKFIIVIVLYALIYFYQRFFDKKVIFA
LIMASLICFIWLGGLNPILFNIKFYIFRDIADSGDAVFKFFNVNQTIRESSAIDFNTVVTRISGHLIV
FLVSIIGYILFIKNNKILLLTLPILFLGLMSFKSGLRFTIYSVPVMALGFGYFVMYCFAKIDIKDRFL
GYVFLFVVTFSALYPSLKHIYDYKVFPVFTHSEVESLDNLKNIAKREDYVLSWWDYGYPIRYYSDVKT
LIDGGKHLGSDNFAVSFALGSDQNSSANMARLEVEYTEKNYEEKFGLNLKKMMKDYNATNVNEFLLSL
KDENLTLPKQTRDIYYYLPDRMIYIYPIVLDFSRLDLTTGQEFAQPFFMVSERFSATNDNQIMLNNNV
ILSNDGTKLSINGNSYSVNTYVETSYDQNEKLNVNYFNIDPNSNFYVIFMKDYLRILVLDKTLYDSAY
IQLFVLENYDKNLFEPVILNGSTKIYKLKK

SEQUENCE LISTING

```
<160> NUMBER OF SEQ ID NOS: 41

<210> SEQ ID NO 1
<211> LENGTH: 2142
<212> TYPE: DNA
<213> ORGANISM: Campylobacter jejuni

<400> SEQUENCE: 1

atgttgaaaa aagagtattt aaaaaaccct tatttagttt tgtttgcgat gattatatta      60

gcttatgttt ttagtgtatt ttgcaggttt tattgggttt ggtgggcaag tgagtttaat     120

gagtattttt tcaataatca gttaatgatc atttcaaatg atggctatgc ttttgctgag     180

ggcgcaagag atatgatagc aggttttcat cagcctaatg atttgagtta ttatggatct     240

tctttatccg cgcttactta ttggctttat aaaatcacac ctttttcttt tgaaagtatc     300

attttatata tgagtacttt tttatcttct ttggtggtga ttcctactat tttgctagct     360

aacgaataca aacgtccttt aatgggcttt gtagctgctc ttttagcaag tatagcaaac     420

agttattata atcgcactat gagtgggtat tatgatacgg atatgctggt aattgttttg     480

cctatgttta ttttattttt tatggtaaga atgattttaa aaaaagactt tttttcattg     540

attgccttgc cgttatttat aggaatttat ctttggtggt atccttcaag ttatacttta     600

aatgtagctt taattggact ttttttaatt tatacactta tttttcatag aaaagaaaag     660

atttttttata tagctgtgat tttgtcttct cttactcttt caaatatagc atggttttat     720

caaagtgcca ttatagtaat actttttgct ttattcgcct tagagcaaaa acgcttaaat     780

tttatgatta taggaatttt aggtagtgca actttgatat ttttgatttt aagtggtggg     840

gttgatccta tactttatca gcttaaattt tatatttta gaagtgatga aagtgcgaat     900

ttaacgcagg gctttatgta ttttaatgtc aatcaaacca tacaagaagt tgaaaatgta     960

gatcttagcg aatttatgcg aagaattagt ggtagtgaaa ttgttttttt gttttctttg    1020

tttggttttg tatggctttt gagaaaacat aaaagtatga ttatggcttt acctatattg    1080

gtgcttgggt ttttagcctt aaaaggggg  cttagattta ccatttattc tgtacctgta    1140

atggccttag gatttggttt tttattgagc gagtttaagg ctataatggt taaaaaatat    1200

agccaattaa cttcaaatgt ttgtattgtt tttgcaacta ttttgacttt agctccagta    1260

tttatccata tttacaacta taaagcgcca acagtttttt ctcaaaatga agcatcatta    1320

ttaaatcaat taaaaaatat agccaataga gaagattatg tggtaacttg gtgggattat    1380

ggttatcctg tgcgttatta tagcgatgtg aaaactttag tagatggtgg aaagcattta    1440

ggtaaggata attttttccc ttcttttgct ttaagcaaag atgaacaagc tgcagctaat    1500

atggcaagac ttagtgtaga atatacagaa aaaagctttt atgctccgca aaatgatatt    1560

ttaaaaaacag acattttgca agccatgatg aaagattata atcaaagcaa tgtggatttg    1620

tttctagctt cattatcaaa acctgatttt aaaatcgata cgccaaaaac tcgtgatatt    1680

tatctttata tgcccgctag aatgtctttg atttttcta cggtggctag tttttctttt    1740

attaatttag atacaggagt tttggataaa ccttttacct ttagcacagc ttatccactt    1800

gatgttaaaa atggagaaat ttatcttagc aacggagtgg ttttaagcga tgattttaga    1860
```

-continued

```
agttttaaaa taggtgataa tgtggtttct gtaaatagta tcgtagagat taattctatt   1920

aaacaaggtg aatacaaaat cactccaatt gatgataagg ctcagtttta tatttttat   1980

ttaaaggata gtgctattcc ttacgcacaa tttattttaa tggataaaac catgtttaat   2040

agtgcttatg tgcaaatgtt ttttttagga aattatgata agaatttatt tgacttggtg   2100

attaattcta gagatgctaa ggtttttaaa cttaaaattt aa                      2142


<210> SEQ ID NO 2
<211> LENGTH: 713
<212> TYPE: PRT
<213> ORGANISM: Campylobacter jejuni

<400> SEQUENCE: 2

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
```

-continued

```
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 3
<211> LENGTH: 5
<212> TYPE: PRT
<213> ORGANISM: Artificial Sequence
```

-continued

```
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 3

Asp Xaa Asn Xaa Ser
1               5


<210> SEQ ID NO 4
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 4

Asp Xaa Asn Xaa Thr
1               5


<210> SEQ ID NO 5
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 5

Glu Xaa Asn Xaa Ser
1               5


<210> SEQ ID NO 6
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 6

Glu Xaa Asn Xaa Thr
1               5


<210> SEQ ID NO 7
<211> LENGTH: 19
<212> TYPE: DNA
<213> ORGANISM: Artificial Sequence
<220> FEATURE:
<223> OTHER INFORMATION: recognition sequence

<400> SEQUENCE: 7

ctgtctcttg atcagatct                                                19
```

<210> SEQ ID NO 8
<211> LENGTH: 19
<212> TYPE: DNA
<213> ORGANISM: Artificial Sequence
<220> FEATURE:
<223> OTHER INFORMATION: recognition sequence

<400> SEQUENCE: 8
acttgtgtat aagagtcag 19

<210> SEQ ID NO 9
<211> LENGTH: 33
<212> TYPE: DNA
<213> ORGANISM: Artificial Sequence
<220> FEATURE:
<223> OTHER INFORMATION: recombination site sequence

<400> SEQUENCE: 9
ataacttcgt ataatgtatg ctatacgaag tag 33

<210> SEQ ID NO 10
<211> LENGTH: 34
<212> TYPE: DNA
<213> ORGANISM: Artificial Sequence
<220> FEATURE:
<223> OTHER INFORMATION: recombination site sequence

<400> SEQUENCE: 10
ataacttcgt ataatgtatg ctatacgaag ttat 34

<210> SEQ ID NO 11
<211> LENGTH: 48
<212> TYPE: DNA
<213> ORGANISM: Artificial Sequence
<220> FEATURE:
<223> OTHER INFORMATION: recognition site sequences

<400> SEQUENCE: 11
gaagttccta ttccgaagtt cctattctct agaaagtata ggaacttc 48

<210> SEQ ID NO 12
<211> LENGTH: 48
<212> TYPE: DNA
<213> ORGANISM: Artificial Sequence
<220> FEATURE:
<223> OTHER INFORMATION: recognition site sequence

<400> SEQUENCE: 12
gaagtaccta ttccgaagtt cctattctct agaaagtata ggaacttc 48

<210> SEQ ID NO 13
<211> LENGTH: 1032
<212> TYPE: DNA
<213> ORGANISM: Artificial Sequence
<220> FEATURE:
<223> OTHER INFORMATION: recombinase

<400> SEQUENCE: 13
atgtccaatt tactgaccgt acaccaaaat ttgcctgcat taccggtcga tgcaacgagt 60
gatgaggttc gcaagaacct gatggacatg ttcagggatc gccaggcgtt ttctgagcat 120
acctggaaaa tgcttctgtc cgtttgccgg tcgtgggcgg catggtgcaa gttgaataac 180
cggaaatggt ttcccgcaga acctgaagat gttcgcgatt atcttctata tcttcaggcg 240
cgcggtctgg cagtaaaaac tatccagcaa catttgggcc agctaaacat gcttcatcgt 300
cggtccgggc tgccacgacc aagtgacagc aatgctgttt cactggttat gcggcggatc 360
cgaaaagaaa acgttgatgc cggtgaacgt gcaaaacagg ctctagcgtt cgaacgcact 420
gatttcgacc aggttcgttc actcatggaa aatagcgatc gctgccagga tatacgtaat 480
ctggcatttc tggggattgc ttataacacc ctgttacgta tagccgaaat tgccaggatc 540
agggttaaag atatctcacg tactgacggt gggagaatgt taatccatat tggcagaacg 600
aaaacgctgg ttagcaccgc aggtgtagag aaggcactta gcctgggggt aactaaactg 660
gtcgagcgat ggatttccgt ctctggtgta gctgatgatc cgaataacta cctgttttgc 720
cgggtcagaa aaaatggtgt tgccgcgcca tctgccacca gccagctatc aactcgcgcc 780
ctggaaggga tttttgaagc aactcatcga ttgatttacg gcgctaagga tgactctggt 840
cagagatacc tggcctggtc tggacacagt gcccgtgtcg gagccgcgcg agatatggcc 900
cgcgctggag tttcaatacc ggagatcatg caagctggtg gctggaccaa tgtaaatatt 960
gtcatgaact atatccgtaa cctggatagt gaaacagggg caatggtgcg cctgctggaa 1020
gatggcgatt ag 1032

<210> SEQ ID NO 14
<211> LENGTH: 1272
<212> TYPE: DNA
<213> ORGANISM: Artificial Sequence
<220> FEATURE:
<223> OTHER INFORMATION: recombinase FLP FRT system

<400> SEQUENCE: 14
atgagccagt tcgatatcct gtgtaaaacc ccgcctaagg tgcttgttcg tcagtttgtg 60
gaaaggtttg aaagaccttc aggtgagaaa atagcatcct gtgctgctga actaacctat 120
ttatgttgga tgattacaca taacggaaca gcaatcaaga gagccacatt catgagctat 180
aatactatca taagcaattc gctgagtttc gatattgtca ataaatcact ccagtttaaa 240
tacaagacgc aaaaagcaac aattctggaa gcctcattaa agaaattgat tcctgcttgg 300
gaatttacaa ttattcctta caacggacaa aaacatcaat ctgatatcac tgatattgta 360
agtagtttgc aattacagtt cgaatcatcg gaagaagcag ataagggaaa tagccacagt 420
aaaaaaatgc ttaaagcact tctaagtgag ggtgaaagca tctgggagat cactgagaaa 480
atactaaatt cgtttgagta tacttcgaga tttacaaaaa caaaaacttt ataccaattc 540
ctcttcctag ctactttcat caattgtgga agattcagcg atattaagaa cgttgatccg 600
aaatcattta aattagtcca aaataagtat ctgggagtaa taatccagtg tttagtgaca 660
gagacaaaga caagcgttag taggcacata tacttcttta gcgcaagggg taggatcgat 720
ccacttgtat atttggatga atttttgagg aattctgaac cagtcctaaa acgagtaaat 780
aggaccggca attcttcaag caataaacag gaataccaat tattaaaaga taacttagtc 840
agatcgtaca ataaagcttt gaagaaaaat gcgccttatc cgatctttgc tataaaaaat 900
ggcccaaaat ctcacattgg aagacatttg atgacctcat ttctttcaat gaagggccta 960
acggagttga ctaatgttgt gggaaattgg agcgataagc gtgcttctgc cgtggccagg 1020
acaacgtata ctcatcagat aacagcaata cctgatcact acttcgcact agtttctcgg 1080
tactatgcat atgatccaat atcaaaggaa atgatagcat tgaaggatga gactaatcca 1140
attgaggagt ggcagcatat agaacagcta aagggtagtg ctgaaggaag catacgatac 1200
cccgcatgga atgggataat atcacaggag gtactagact acctttcatc ctacataaat 1260
agacgcatat ag 1272

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
ttttgcggcc gcttctacgt gttccgcttc c 31

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
ttttgcggcc gcattgcgtt gcgctcactg c 31

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
ttttgcggcc gcttctcatg tttgacagct tatc 34

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
ttttgcggcc gcagcgagtc agtgagcgag g 31

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
ttttgcgatc gcttctcatg tttgacagct tatc 34

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
ttttaggcct agcgagtcag tgagcgagg 29

<210> SEQ ID NO 21
<211> LENGTH: 603
<212> TYPE: DNA
<213> ORGANISM: Artificial Sequence
<220> FEATURE:
<223> OTHER INFORMATION: pJCUSA1

<400> SEQUENCE: 21
ggccgcctag gccgcggccg cctacttcgt atagcataca ttatacgaag ttatgtctga 60
cgctcagtgg aacgacgcgt aactcacgtt aagggatttt ggtcatgatc agcacgttga 120
caattaatca tcggcatagt atatcggcat agtataatac gacaaggtga ggaactaaaa 180
catggccaag ttgaccagtg ccgttccggt gctcaccgcg cgcgacgtcg ccggagcggt 240
cgagttctgg accgaccggc tcgggttctc ccgggacttc gtggaggacg acttcgccgg 300
tgtggtccgg gacgacgtga ccctgttcat cagcgcggtc caggaccagg tggtgccgga 360
caacaccctg gcctgggtgt gggtgcgcgg cctggacgag ctgtacgccg agtggtcgga 420
ggtcgtgtcc acgaacttcc gggacgcctc cgggccggcc atgaccgaga tcggcgagca 480
gccgtggggg cgggagttcg ccctgcgcga cccggccggc aactgcgtgc acttcgtggc 540
cgaggagcag gactgaataa cttcgtatag catacattat acgaagttat ggccgcctag 600
gcc 603

<210> SEQ ID NO 22
<211> LENGTH: 2133
<212> TYPE: DNA
<213> ORGANISM: Campylobacter sputorum

<400> SEQUENCE: 22
atgtcaaatt ttaatttcgc taaatttcta aataaattac ctagactttc taaacatact 60
attttaatga ttgttttagc tgtttgtttt gggatatttt gcagatttta ctgggtagtt 120
tgggctagtg cttatccgca ttttatatgg aatgatcagc ttatgataag cacaaatgac 180
ggatatgcat ttgctgaggg cacaagagat atgatagctg gttttcatca accaaacgat 240
ctttcttact atggctcatc tctttcgacg cttagcatgt ggttatataa cattttgcca 300
ttttcattag aaactatact tttgtatatg agtacatttt tatctccact cttagctgtg 360
cctttgatac ttataggtaa agaactaaac gcttcaaaag cgggttttat agctgcactt 420
ctagctatta ttgcaaatag ttattataat agaacaatga gtggatatta cgatacggat 480
atgctaaata tcactcttcc tatgatggtt ttttggagca taacaagact tgttcaaaga 540
aaagagagag taaatttaat atttattccg gtttttatgg cgatatatgg atggtggtat 600
ccatcttctt actcactatt acttgccatg attggaatgt ttttttata taccattgtt 660 tttgaaagat acgaaaaact aaactatgaa gctatggttt ttatgatttt agcaatcaca 720
agcttttcta tacaaattaa atttattata gttattgttt tgtatgcttt aatctatttt 780
taccaaagat tttttgataa aaaagtaata tttgcattaa ttatggcttc gttaatatgc 840
tttatatggc ttggcgggct aaaccctata ctttttaaca ttaaatttta tatatttaga 900
gacattgcag atagcggtga tgctgttttt aaattttca atgtaaatca aacaataaga 960
gaaagttctg cgatagattt taacacagtt gtaactagga ttagcgggca tttaatagta 1020
tttttggtat ctattatagg atatatttta tttataaaaa acaataaaat tttactacta 1080
actttaccga ttctgttttt gggtcttatg tcatttaaaa gtggtttaag atttacaata 1140
tactcagttc cagtaatggc tcttggtttt ggctattttg ttatgtattg ttttgcaaaa 1200
atagatataa aagatcgttt tttaggttat gtgtttttat ttgttgtaac atttagtgca 1260
ttatatccat ctttaaaaca tatttatgat tataaagtat ttcctgtttt tacacatagc 1320

-continued

```
gaagttgaaa gtttggataa tttaaaaaat attgcaaaaa gagaagatta tgtgctttct   1380

tggtgggatt atggttatcc gatcagatat tattcagatg taaaaactct catagatgga   1440

ggaaaacatc ttggaagtga taacttcgcc gttagctttg cacttggaag cgatcaaaat   1500

agctctgcaa atatggcaag attagaagtt gaatatacag aaaaaaatta tgaagaaaaa   1560

tttggattaa atttaaaaaa gatgatgaaa gattataatg ctacaaatgt taatgagttt   1620

ttattatcat taaaagatga aaatttaact ctgccaaagc aaacaagaga tatttattac   1680

tatttaccag atagaatgat atacatatat ccgatagtgc tagatttttc tagacttgat   1740

ttgacaacag ggcaagaatt tgcccagccg ttttttatgg ttagtgagag attttcagct   1800

acaaatgata atcaaataat gttaaataac aatgtcatat taagtaatga tggcactaaa   1860

ttatcgataa atggcaactc ttatagtgta aatacatatg ttgaaacaag ttatgatcaa   1920

aacgaaaaat taaatgtaaa ttattttaac atagatccaa atagcaattt ttatgtgatt   1980

tttatgaaag attatttgag aattttggtt ttagataaaa ctttgtatga tagtgcgtat   2040

attcaacttt ttgtattaga aaattatgat aaaaatttat ttgaaccagt gattttaaac   2100

ggatcaacta aaatttataa actcaaaaaa tga                                 2133
```

```
<210> SEQ ID NO 23
<211> LENGTH: 710
<212> TYPE: PRT
<213> ORGANISM: campylobacter sputorum

<400> SEQUENCE: 23

Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Gln Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Ser Ser Leu Ser Thr Leu Ser Met Trp Leu Tyr
                85                  90                  95

Asn Ile Leu Pro Phe Ser Leu Glu Thr Ile Leu Leu Tyr Met Ser Thr
            100                 105                 110

Phe Leu Ser Pro Leu Leu Ala Val Pro Leu Ile Leu Ile Gly Lys Glu
        115                 120                 125

Leu Asn Ala Ser Lys Ala Gly Phe Ile Ala Ala Leu Leu Ala Ile Ile
    130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Phe Leu Tyr Thr Ile Val Phe Glu Arg Tyr
    210                 215                 220

Glu Lys Leu Asn Tyr Glu Ala Met Val Phe Met Ile Leu Ala Ile Thr
```

-continued

```
225                 230                 235                 240

Ser Phe Ser Ile Gln Ile Lys Phe Ile Ile Val Ile Val Leu Tyr Ala
                245                 250                 255

Leu Ile Tyr Phe Tyr Gln Arg Phe Phe Asp Lys Lys Val Ile Phe Ala
            260                 265                 270

Leu Ile Met Ala Ser Leu Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Ala Val Phe Lys Phe Phe Asn Val Asn Gln Thr Ile Arg
305                 310                 315                 320

Glu Ser Ser Ala Ile Asp Phe Asn Thr Val Val Thr Arg Ile Ser Gly
                325                 330                 335

His Leu Ile Val Phe Leu Val Ser Ile Ile Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
    370                 375                 380

Val Met Ala Leu Gly Phe Gly Tyr Phe Val Met Tyr Cys Phe Ala Lys
385                 390                 395                 400

Ile Asp Ile Lys Asp Arg Phe Leu Gly Tyr Val Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asn Leu
        435                 440                 445

Lys Asn Ile Ala Lys Arg Glu Asp Tyr Val Leu Ser Trp Trp Asp Tyr
    450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510

Thr Glu Lys Asn Tyr Glu Glu Lys Phe Gly Leu Asn Leu Lys Lys Met
        515                 520                 525

Met Lys Asp Tyr Asn Ala Thr Asn Val Asn Glu Phe Leu Leu Ser Leu
    530                 535                 540

Lys Asp Glu Asn Leu Thr Leu Pro Lys Gln Thr Arg Asp Ile Tyr Tyr
545                 550                 555                 560

Tyr Leu Pro Asp Arg Met Ile Tyr Ile Tyr Pro Ile Val Leu Asp Phe
                565                 570                 575

Ser Arg Leu Asp Leu Thr Thr Gly Gln Glu Phe Ala Gln Pro Phe Phe
            580                 585                 590

Met Val Ser Glu Arg Phe Ser Ala Thr Asn Asp Asn Gln Ile Met Leu
        595                 600                 605

Asn Asn Asn Val Ile Leu Ser Asn Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655
```

Phe Tyr Val Ile Phe Met Lys Asp Tyr Leu Arg Ile Leu Val Leu Asp
660 665 670

Lys Thr Leu Tyr Asp Ser Ala Tyr Ile Gln Leu Phe Val Leu Glu Asn
675 680 685

Tyr Asp Lys Asn Leu Phe Glu Pro Val Ile Leu Asn Gly Ser Thr Lys
690 695 700

Ile Tyr Lys Leu Lys Lys
705 710

<210> SEQ ID NO 24
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 24

Asp Val Asn Val Thr
1 5

<210> SEQ ID NO 25
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 25

Glu Val Asn Ala Thr
1 5

<210> SEQ ID NO 26
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 26

Asp Gln Asn Ala Thr
1 5

<210> SEQ ID NO 27
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 27

Asp Asn Asn Asn Thr
1 5

<210> SEQ ID NO 28
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 28

Asp Asn Asn Asn Ser
1 5

<210> SEQ ID NO 29
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 29

Asp Gln Asn Arg Thr
1               5

<210> SEQ ID NO 30
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 30

Glu Asn Asn Phe Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 31

Asp Ser Asn Ser Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 32

Asp Gln Asn Ile Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 33

Asp Gln Asn Val Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 34

Asp Asn Asn Val Ser
1               5

<210> SEQ ID NO 35

<211> LENGTH: 5
<212> TYPE: PRT
<213> ORGANISM: Artificial Sequence
<220> FEATURE:
<223> OTHER INFORMATION: Amino Acid Motif

<400> SEQUENCE: 35

Asp Tyr Asn Val Ser
1 5

<210> SEQ ID NO 36
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 36

Asp Phe Asn Val Ser
1 5

<210> SEQ ID NO 37
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 37

Asp Phe Asn Ala Ser
1 5

<210> SEQ ID NO 38
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 38

Asp Phe Asn Ser Ser
1 5

<210> SEQ ID NO 39
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 39

Asp Val Asn Ala Thr
1 5

<210> SEQ ID NO 40
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 40

Asp Phe Asn Val Thr
1 5

<210> SEQ ID NO 41
<211> LENGTH: 5

-continued

```
<212> TYPE: PRT
<213> ORGANISM: Artificial Sequence
<220> FEATURE:
<223> OTHER INFORMATION: Amino Acid Motif

<400> SEQUENCE: 41

Asp Val Asn Ala Ser
1               5
```

GLYCOSYLATION METHOD

CROSS REFERENCE TO RELATED APPLICATIONS

This is the U.S. National Stage of International Application No. PCT/GB2014/050133, filed Jan. 17, 2014, which was published in English under PCT Article 21(2), which in turn claims the benefit of United Kingdom Application Nos. 1300956.8, filed Jan. 18, 2013, 1301023.6, filed Jan. 21, 2013, and 1309068.3, filed May 20, 2013.

FIELD OF THE INVENTION

The invention relates to microbial host cells engineered to produce glycoconjugate vaccines by stable integration of an oligosaccharyltransferase and optionally a carrier protein into the host's genome, wherein expression of the oligosaccharyltransferase is regulated.

BACKGROUND OF THE INVENTION

Bioavailability and bioactivity of small molecules, peptides, proteins or nucleic acids can be altered by glycosylation. Glycosylation is the transfer of an activated sugar moiety from a donor to an acceptor molecule and is catalysed by glycosyltransferases. Glycosylation of proteins occurs either co- or post-translationally by which a sugar moiety is attached to a nitrogen of asparagine or arginine side-chains forming N-linked glycans, or to the hydroxy oxygen of serine, threonine, tyrosine, lysine, or proline side-chains forming O-linked glycans, or less common forming C-linked glycans where the sugar is added to carbon on a tryptophan side-chain.

N-linked glycosylation is the most common post-translational modification and is carried out in the endoplasmic reticulum of eukaryotic cells. N-linked glycosylation can be of two main types; high mannose oligosaccharides which have two N-acetylglucosamines and complex oligosaccharides which include other types of sugar groups. The peptide motif contained in glycosylated polypeptides is Asn-X-Ser or Asn-X-Thr where X is any amino acid except proline. This is catalysed by the enzyme oligosaccharyltransferase [OT]; see Yan & Lennarz J. Bioi. Chem., Vol. 280 (5), 3121-3124 (2005). OT catalyses the transfer of an oligosaccharyl moiety (Glc3Man9GlcNAc2) from the dolichol-linked pyrophosphate donor to the side chain of an Asn. A pentasaccharide core is common to all N-linked oligosaccharides and serves as the foundation for a wide variety of N-linked oligosaccharides. O-linked glycosylation is less common. Serine or threonine residues are linked via their side chain oxygen to sugars by a glycosidic bond. Usually N-acetylglucosamine is attached in this way to intracellular proteins.

Most bacterial glycoproteins are associated with the bacterial cell surface or are secreted, suggesting a role for glycoproteins in the interaction with the host's immune system. Studies on the gram negative pathogenic bacterium *Campylobacter jejuni* identified a gene cluster involved in the synthesis of lipo-oligosaccharides and N-linked glycoproteins. The protein glycosylation locus, a cluster of 12 genes comprising pglA-pglG, is involved in the glycosylation of over 30 glycoproteins. Interestingly, these genes can be used to modify lipopolysaccharide structures in *Escherichia coli* providing a genetic tool to express heterologous recombinant glycoproteins. Studies performed with *C. jejuni* carrying mutations in the pglB and pglE genes showed impaired colonisation abilities in mice.

Polysaccharide antigens interact directly with B cells and induce antibody synthesis in the absence of T-cells. This T-cell independent immune response is limited as antibody production is low and is not normally boosted by re-immunisation. The antibody isotypes are dominated bylg-Mand IgG2, which are short lived and are generally of low affinity for a specific antigen. The ability to enhance the immunogenicity of polysaccharide antigens can be achieved by conjugation of the polysaccharide to a protein carrier. Glycoconjugate vaccines for *Streptococcus pneumoniae, Neisseria meningitidis* and *Haemophilus influenzae* are currently licensed for human use and are produced by linking the capsule (or other bacterial glycan-based structure such as lipooligosaccharide) from these bacteria to a protein toxoid. Whilst these vaccines provide a good level of immunity they are expensive and difficult to produce, requiring the purification of the glycan from the pathogenic organisms and chemical linkage to the carrier protein. The use of organic systems represents a more rapid and economical method for the production of glycoconjugates.

The production of glyconjugates in an *E. coli* expression system requires the co-expression of three genes ["tri-plasmid"]: an acceptor protein, a polysaccharide biosynthetic locus and, for the coupling reaction, an oligosaccharyltransferase enzyme. Optimisation of co-expression in just one host is a lengthy process as it requires a tailored choice of the plasmids and optimised growth and expression conditions which are dependent on several factors. Additionally, the yield of glycoconjugates using such expression systems are often very low, which makes it commercial not viable.

The tri-plasmid system has a number of disadvantages. Compatible origins of plasmid replication need to be combined, a process that can take several months and restricts the choice of available plasmids. The use of three plasmids represents a considerable metabolic burden on the host bacterial strain and often the contents of one of the plasmids fail to express. Three different antibiotic selection markers for each of the plasmids need to be combined. This represents another burden on the host strain and clashes often result in sub-cloning of antibiotic resistance genes to find combinations that match. Additionally, some antibiotics resistance combinations are legally forbidden in some strains. Some glycosyltransferases [e.g. PglB enzyme] responsible for linking the glycan to the protein has multiple transmembrane domains and is toxic to bacterial cells. Once expressed it has been found to reduce the growth of the host bacterial strain considerably. This significantly inhibits glycoconjugate yield. Heterologous expression of the polysaccharide coding genes and the resulting enzymes that are generated can result in high levels of toxicity to the host. Therefore, with some glycans it is impossible to find a tri-plasmid combination that allows for glycoconjugate production.

An example of the tri-plasmid system is disclosed in WO2009/104074 which describes the optimised production of conjugates comprising a protein carrier linked to an antigenic polysaccharide in an *E. coli* tri-plasmid expression system. The yield using this system is increased significantly by growing cells carrying three genes on two plasmids in a bioreactor under carefully monitored growth condition.

The present disclosure relates to a method providing the stable integration of genes into a bacterial genome for the production of glycoconjugates controlled by constitutive and regulated promoter elements which results in high yields of glycoconjugate. The application discloses also a method for the genetic manipulation of transposons facilitating easy and efficient preparation of the transposable element which allows integration of genes into the genome in one single step and additionally comprising also a tool which permits easy removal of the resistance marker once the gene of interest has integrated into the host genome.

STATEMENTS OF THE INVENTION

According to an aspect of the invention there is provided an isolated nucleic acid molecule comprising a transcription cassette adapted for expression in a bacterial host cell said cassette comprising: a nucleotide sequence encoding a glycosyltransferase enzyme wherein the expression of said enzyme is regulatable and a nucleotide sequence encoding an acceptor polypeptide for an oligosaccharide or monosaccharide wherein the acceptor polypeptide includes an amino acid sequence motif which is a substrate for the glycosyltransferase enzyme.

In a preferred embodiment of the invention the transcription cassette further comprises a regulatable promoter functionally linked to at least the nucleotide sequence encoding said glycosyltransferase enzyme.

In a preferred embodiment of the invention said promoter includes an inducible nucleotide element conferring regulatable expression in response to an inducer.

In a preferred embodiment of the invention said inducer is IPTG.

In an alternative embodiment of the invention said promoter includes a repressible nucleotide element conferring regulatable expression in response to a repressor.

In a preferred embodiment of the invention said repressor is the Laclq repressor.

Bacterial expression systems that utilize inducers and repressors of gene expression are well known in the art and include modifications that are well established which enhance induction or repression of gene expression. For example is laclq carries a mutation in the promoter region of the lacl gene that results in increased transcription and higher levels of Lac repressor within the cells. Moreover, the Ptac, a strong hybrid promoter composed of the −35 region of the trp promoter and the −10 region of the lacUV5 promoter/operator and is strongly inducible.

In a preferred embodiment of the invention said glycosyltransferase is selected from the group consisting of: an oligosaccharyltransferase, a glucosyltransferase, a mannosyltransferase or a glucuronosyltransferase.

In a preferred embodiment of the invention said glycosyltransferase is an oligosaccharyltransferase, In a preferred embodiment of the invention said nucleic acid molecule encodes an oligosaccharyltransferase selected from the group consisting of:

i) a nucleic acid molecule comprising a nucleotide sequence as set forth in SEQ ID NO 1 or SEQ ID NO: 22;
ii) a nucleic acid molecule the complimentary strand of which hybridizes under stringent hybridization to SEQ ID NO: 1 or SEQ ID NO: 22 and encodes an oligosaccharyltransferase that recognizes the amino acid motif: D/E-X-N-X-S/T, wherein X is any amino acid except proline;
iii) a nucleic acid molecule comprising a nucleotide sequence that is degenerate with respect to the nucleotide sequence in SEQ ID NO: 1 and which encodes a polypeptide comprising an amino acid sequence as represented in SEQ ID NO:2;
iv) a nucleic acid molecule comprising a nucleotide sequence that is degenerate with respect to the nucleotide sequence in SEQ ID NO: 22 and which encodes a polypeptide comprising an amino acid sequence as represented in SEQ ID NO: 23;
v) a variant sequence that varies from the amino acid sequences set forth in SEQ ID NO: 2 or 23 and which has oligosaccharyltransferase activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand.

The following is an exemplary set of hybridization conditions and is not limiting.

Very High Stringency (Allows Sequences that Share at Least 90% Identity to Hybridize)

i) Hybridization: 5×SSC at 65° C. for 16 hours
ii) Wash twice: 2×SSC at room temperature (RT) for 15 minutes each
iii) Wash twice: 0.5×SSC at 65° C. for 20 minutes each High Stringency (Allows Sequences that Share at Least 80% Identity to Hybridize)

i) Hybridization: 5×-6×SSC at 65° C.-70° C. for 16-20 hours
ii) Wash twice: 2×SSC at RT for 5-20 minutes each
iii) Wash twice: 1×SSC at 55° C.-70° C. for 30 minutes each Low Stringency (Allows Sequences that Share at Least 50% Identity to Hybridize)

i) Hybridization: 6×SSC at RT to 55° C. for 16-20 hours
ii) Wash at least twice: 2×-3×SSC at RT to 55° C. for 20-30 minutes each.

In a preferred embodiment of the invention said acceptor polypeptide includes the amino acid motif: Asn-X-Ser or Asn-X-Thr where X is any amino acid except proline.

In an alternative embodiment of the invention said acceptor polypeptide includes the amino acid motif: D/E-X-N-X-S/T, wherein X is any amino acid except proline.

In an alternative preferred embodiment of the invention said acceptor polypeptide including the amino acid motif D/E-X-N-X-S/T, wherein X is any amino acid except proline is selected from the group consisting of: DVNVT (SEQ ID NO: 24), EVNAT (SEQ ID NO: 25), DQNAT (SEQ ID NO: 26), DNNNT (SEQ ID NO: 27), DNNNS (SEQ ID NO: 28), DQNRT (SEQ ID NO: 29), ENNFT (SEQ ID NO: 30), DSNST (SEQ ID NO: 31), DQNIS (SEQ ID NO: 32), DQNVS (SEQ ID NO: 33), DNNVS (SEQ ID NO: 34), DYNVS (SEQ ID NO: 35), DFNVS (SEQ ID NO: 36), DFNAS (SEQ ID NO: 37), DFNSS (SEQ ID NO: 38), DVNAT (SEQ ID NO: 39), DFNVT (SEQ ID NO: 40) or DVNAS (SEQ ID NO: 41).

In a further preferred embodiment of the invention said transcription cassette comprises a nucleotide sequence that encodes one or more polysaccharide biosynthetic genes.

In a preferred embodiment of the invention said one or more biosynthetic genes are selected from the group consisting of the capsular polysaccharide or O antigen coding regions.

In a preferred embodiment of the invention said transcription cassette is adapted by the provision of one or more inverted repeat nucleotide sequences that are transposase recognition sequences.

In a preferred embodiment of the invention said recognition sequence comprises or consists essentially of the nucleotide sequences:

(SEQ ID NO:7) 5'-CTGTCTCTTGATCAGATCT-3' at the I end; and (SEQ ID NO: 8) 5'-ACTTGTGTATAAGAGTCAG-3', at the O end of the miniTn5 transposon.

In a preferred embodiment of the invention said transcription cassette further comprises a nucleotide sequence encoding a bacterial resistance marker gene.

In a preferred embodiment of the invention said bacterial resistance gene confers resistance to an antibiotic.

In a preferred of the invention said antibiotic is selected from the group consisting of: kanamycin, chloramphenicol, ampicillin, rifampicin, tetracycline, carbenecillin or Zeocin® [phleomycin: cas code 1006-33-0].

In a preferred embodiment of the invention said antibiotic is Zeocin®.

A skilled artisan is familiar with the use of different antibacterial markers. There are several classes of antibiotics targeting either the bacterial cell wall, cell membrane, interfere with essential bacterial enzymes, or target protein synthesis. Further, antibacterial antibiotics can target specific types of bacteria, such as Gram-negative or Gram-positive bacteria, whereas broad-spectrum antibiotics affect a wide range of bacteria.

In a preferred embodiment of the invention said bacterial resistance marker gene is adapted by the provision of 5' and 3' flanking nucleotide sequences that include recombination sites.

In a preferred embodiment of the invention said recombination sites comprise or consist essentially of the nucleotide sequence:

```
5' end loxP sequence:
                                         (SEQ ID NO: 9)
5'-ATAACTTCGTATAATGTAT GCTATACGAA GTAG-3'.

3' end loxP sequence:
                                         (SEQ ID NO: 10)
5'-ATAAC TTCGTATAATGTATGCTATA CGAAGTTAT-3'
for the CRE LOX system or

                                         (SEQ ID NO: 11)
5'-GAAGT TCCTATTCCG AAGTTCCTAT

TCTCTAGAAAGTATAGGAAC TTC-3'
and

                                         (SEQ ID NO: 12)
5'-GAAGTACCTATTC CGAAGTTCCT ATTCTCTAGA

AAGTATAGGA ACTTC-3'
for the FRT FLP system.
```

According to a further aspect of the invention there is provided a vector comprising a transcription cassette according to the invention.

In a preferred embodiment of the invention said vector is a plasmid.

In an alternative preferred embodiment of the invention said vector is a transposon.

In a preferred embodiment of the invention said transposon is selected from the group consisting of: Tn5, Tn10, Himar1 and other mariner elements, Tn7, Tn917, Tn916.

In a preferred embodiment of the invention said transposon is Tn5.

According to a further aspect of the invention there is provided a bacterial cell genetically modified with a transcription cassette or vector according to the invention.

In a preferred embodiment of the invention said bacterial cell is a pathogenic Gram-positive bacterial cell.

In a preferred embodiment of the invention said bacterial cell is a pathogenic Gram-negative bacterial cell.

In a preferred embodiment of the invention said bacterial cell is a human pathogen.

In a preferred embodiment of the invention said human pathogen is selected from the group: *Neisseria, Moraxella, Escherichia, Salmonella, Shigella, Pseudomonas, Helicobacter, Legionella, Haemophilus, Klebsiella, Enterobacter, Cronobacter* and *Serratia.*

In a preferred embodiment of the invention said bacterial cell is a non-human pathogen.

In a preferred embodiment of the invention said non-human pathogen is selected from group: *Mannheimia* spp., *Actinobacillus* spp. e.g *Actinobacillus pleuropneumoniae, Pasteurella* spp., *Haemophilus* spp. or *Edwardsiella* spp.

In a preferred embodiment of the invention said bacterial cell is a zoonotic bacterial species.

In a preferred embodiment of the invention said zoonotic bacterial species is selected from the group: *Brucella* spp., *Campylobacter* spp., *Vibrio* spp., *Yersina* spp. and *Salmonella* spp.

According to a further aspect of the invention there is providing a bacterial cell culture comprising a genetically modified bacterial cell according to the invention.

According to an aspect of the invention there is provided a transcription cassette or vector according to the invention for use in the production of one or more glycoconjugates.

According to a further aspect of the invention there is provided a process for the production of one or more glycoconjugates comprising:

i) providing a bacterial cell culture according to the invention;
ii) providing cell culture conditions; and
iii) isolating one or more glyconjugates from the bacterial cell or cell culture medium.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbookBioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington, D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassiumhydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

According to a further aspect of the invention there is provided a method for the stable integration of a transposable element into a bacterial genome comprising:

i) forming a cell culture preparation comprising a bacterial cell and a transposon according to the invention;
ii) incubating the preparation to allow stable integration of the transposon;
iii) selecting bacterial cells that have stably integrated the transposon using culture conditions that select for bacterial cells that are stable integrants; and
iv) cloning bacterial cells that have stably integrated the transposon.

In a preferred method of the invention said selection is an antibiotic selection using a bacterial resistance marker gene.

In a preferred method of the invention the cloned bacterial cells are contacted with a vector comprising a nucleotide sequence that encodes a recombinase that deletes all or part of said bacterial resistance marker gene.

In a preferred embodiment of the invention said recombinase is specific for recombination sites comprising or consisting essentially of the nucleotide sequence set forth in SEQ ID NO: 13 or 14.

According to a further aspect of the invention there is provided a process for the identification of novel glycoconjugates comprising:

i) forming a cell culture preparation comprising a bacterial cell and a transposon according to the invention;
ii) incubating the preparation to allow stable integration of the transposon;
iii) selecting bacterial cells that have stably integrated the transposon using culture conditions that select for bacterial cells that are stable integrants;
iv) cloning bacterial cells that have stably integrated the transposon;
v) isolating glycoconjugates from the cloned bacterial cells or cell culture medium; and
vi) analysing the monosaccharide or polysaccharide content of said isolated glycoconjugate.

According to a further aspect of the invention there is provided a glycoconjugate formed by the process according to the invention.

According to a further aspect of the invention there is provided a method for the delivery of a transposable element to a bacterial cell comprising:

i) providing a vector adapted for high copy number replication in a bacterial cell comprising: a nucleotide sequence of an expression cassette according to the invention, a nucleotide sequence encoding an antibiotic resistance gene cassette wherein the antibiotic resistance gene cassette is flanked by recombination sequences recognized by a recombinase and wherein the cassettes are flanked by restriction sites for excision and delivery into a transposon delivery vector;
ii) providing a transposon delivery vector comprising restriction sites flanked by inverted repeats for delivery of a transposable element to a bacterial cell;
iii) sub-cloning the vector in (i) into the delivery vector in (ii) to provide a modified delivery vector;
iv) transferring the modified delivery vector in (iii) to a bacterial cell and selecting stably integrated bacterial cells by antibiotic resistance;
v) cloning stably integrated bacterial cells; and optionally
vi) transforming the stably integrated bacterial cells with a vector comprising a nucleotide sequence encoding a recombinase that excises the antibiotic resistance genes from the genome of the stably integrated bacterial cells.

Delivery vectors for the transposable elements such as TN5 transposons are known in the art and have significant limitations. For example, the pUT delivery vector includes a R6K origin of replication which limits transformation to *E. coli* strains that are λ pir positive. The development of a high copy number intermediate vector considerably expands the type of bacterial host cell and significantly simplifies the modification of bacterial cells using transposable element.

According to a further aspect of the invention there is provided a kit comprising: a vector adapted for high copy number replication in a bacterial cell wherein the vector comprises: a nucleotide sequence encoding an antibiotic resistance gene cassette and a multiple cloning site for the insertion of an expression cassette according to the invention wherein the antibiotic gene cassette is flanked by recombination sequences recognized by a recombinase and wherein the multiple cloning sites are flanked by restriction sites enabling the excision of the expression cassette.

In a preferred embodiment of the invention said kit further comprises a transposon delivery vector comprising restriction sites flanked with transposase recognition nucleotide sequences.

In a further preferred embodiment of the invention said kit further comprises a recombinase, for example a flippase.

In a preferred embodiment of the invention the kit further includes a bacterial strain or strains compatible with the transposon.

In a preferred embodiment of the invention said kit optionally includes a nucleic acid molecule encoding a glycosyltransferase and a nucleic acid molecule that encodes one or more polysaccharide biosynthetic genes.

Throughout the description and claims of this specification, the words “comprise” and “contain” and variations of the words, for example “comprising” and “comprises”, means “including but not limited to”, and is not intended to (and does not) exclude other moieties, additives, components, integers or steps. “Consisting essentially” means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures;

BRIEF DESCRIPTION OF THE DRAWINGS

FIG. **3*a* PglB nucleotide sequence (SEQ ID NO: 1); FIG. 3*b*** the full length PglB amino acid sequence (SEQ ID NO: 2);

FIG. 4 is the nucleotide sequence encoding for the CRE LOX system recombinase (SEQ ID 13);

FIG. 5 is the nucleotide sequence encoding the FLP FRT recombinase (SEQ ID 14);

FIG. 8 In vitro glycosylation of peptide using pglB expressed in *A. pleuropneumoniae* (App). Reduced mobility of peptide is seen only in test lanes 2 and 9 where membranes from *A. pleuropneumoniae* coding for PglB are used. Lane 3 is a positive control reaction carrying *E. coli* membranes expressing PglB and Lanes 1, 4, 5, 6, 7, 8 and 10 are negative controls demonstrating that peptide shift only occurs when pglB is expressed in *A. pleuropneumoniae* or *E. coli* and combined with the correct glycan.

FIG. 9 is the nucleotide sequence of *Campylobacter sputorum* PglB (SEQ ID NO: 22); and FIG. 10 *Campylobacter sputorum* protein sequence of PglB (SEQ ID NO: 23).

MATERIALS AND METHODS

Construction of pJAN25

Figure 1:
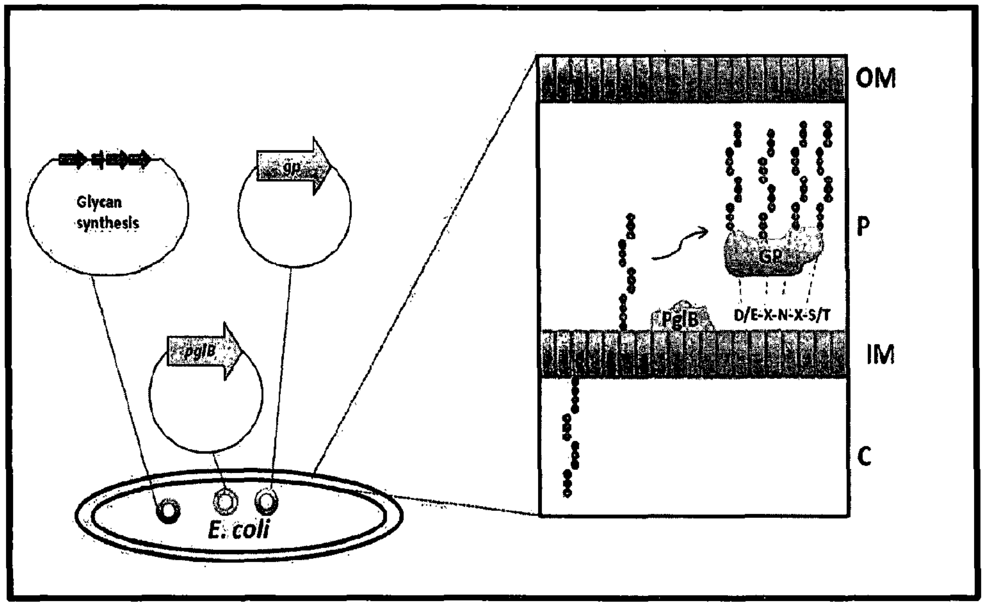
FIG. 1: The tri-plasmid system currently used to generate a glycoconjugate vaccine in *E. coli*. C, cytoplasm; IM, inner membrane; P, periplasm; OM, Outer Membrane.
Figure 2:
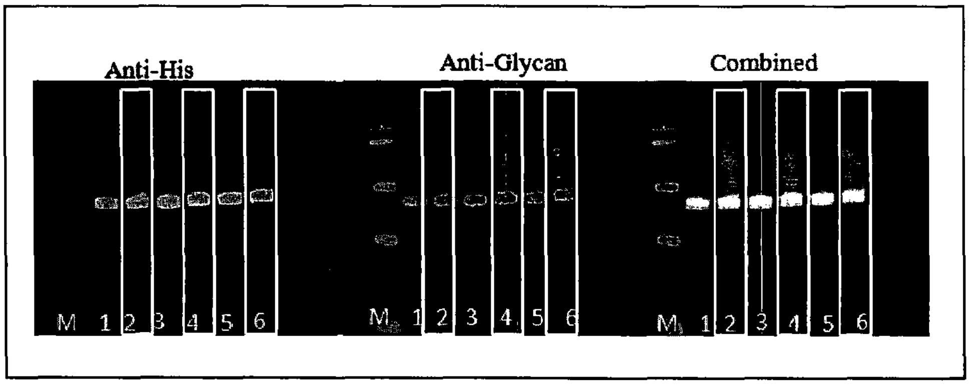
FIG. 2: Chromosomal insertion CjPglB generates superior glycoconjugate yield compared to the standard three plasmid system; AcrA purified from *E. coli* CLM24 carrying chromosomal PglB tested by western blot (lanes 2/4/6) compared to plasmid borne PglB (lanes 1/3/5)

The gene coding for *C. jejuni* PglB was amplified by PCR with the pTac promoter and LacI repressor from plasmid pEXT20 as a template using Pfx Polymerase with (SEQ ID 15: 5'-TTTTGCGGCCGCTTCTACGTGTTCCGCTTCC-3') as forward primer and (SEQ ID 16: 5'-TTTTGCGGCCGCATTGCGTTGCGCTCACTGC-3') reverse primer using the following cycling conditions, 94° C./2 minutes followed by 35 cycles of 94° C. for 30 seconds, 56° C. for 30 seconds and 68° C. for 4 minutes. The PCR product was then cloned in pJET2.0 plasmid (Thermo Scientific U.K.) according to the manufacturer's instructions and named pOST9. The plasmid was maintained in into *E. coli* DH5α (Stratagene U.K.) The vector pOST9 cut with the restriction enzyme NotI (New England Biolabs U.K. Ltd.) and ligated into the unique NotI site in pUTminiTn5km2 resulting in plasmid pJAN25 and maintained in Transformax *E. coli* strain EC100D pir+ (Cambio U.K.).

Construction of pFEB11

The gene coding for *C. jejuni* AcrA was amplified by PCR with the $tet^r$ cassette promoter and chloramphenicol resistance cassette from the plasmid pMH5 as a template using (SEQ ID 17: 5'-TTTTGCGGCCGCTTCTCATGTTTGACAGCTTATC-3') as forward primer and (SEQ ID 18: 5'-TTTTGCGGCCGCAGCGAGTCAGTGAGCGAGG-3') reverse primer using the following cycling conditions, 94° C./2 minutes followed by 35 cycles of 94° C. for 30 seconds, 56° C. for 30 seconds and 68° C. for 2 minutes. The product was cut by NotI and cloned into the unique NotI site in pUTminiTn5km2 resulting in plasmid pFEB11 and maintained in Transformax *E. coli* strain EC100D pir+ (Cambio U.K.).

Construction of pEFNOV19

The gene coding for *C. jejuni* AcrA was amplified by PCR with the tet cassette promoter and cam resistance cassette from the plasmid pMH5 as a template using (SEQ ID 19: 5'-TTTTGCGATCGCTTCTCATGTTTGACAGCTTATC-3') as forward primer and (SEQ ID 20: 5'-TTTTAGGCCTAGCGAGTCAGTGAGCGAGG-3') as reverse primer 94° C./2 minutes followed by 35 cycles of 94° C. for 30 seconds, 56° C. for 30 seconds and 68° C. for 2 minutes. The product was cut by AsisI and StuI (New England Biolabs U.K. Ltd) and cloned in AsisI and StuI digested pJAN25 generating the plasmid pEFNOV19 and maintained in Transformax *E. coli* strain EC100D pir+ (Cambio U.K.).

Construction of pJCUSA1

We devised a novel transposon cargo loading procedure where the cloning experiments are carried out within a modified version of the commercially available high copy number vector pUC57, this modified plasmid has a chloramphenicol resistance cassette in its backbone from plasmid pMH5 and a Zeocin® resistance cassette flanked by loxP sites allowing for downstream removal of antibiotic marker from the final target strain via the introduction of the CRE enzyme. It has a pMB1 origin of replication and thus can be maintained in any *E. coli* strain prior to being cut out and transferred along with the Zeocin® resistance cassette using SfiI restriction enzyme digestion and transfer into the pUT delivery vector thus generating a functional transposon. The sequence of this novel construct is shown below (SEQ ID 21):

```
(SEQ ID 21):
5'GGCCGCCTAGGCCGCGGCCGCCTACTTCGTATAGCATACATTATACGA

AGTTATGTCTGACGCTCAGTGGAACGACGCGTAACTCACGTTAAGGGATT

TTGGTCATGATCAGCACGTTGACAATTAATCATCGGCATAGTATATCGGC

ATAGTATAATACGACAAGGTGAGGAACTAAAACATGGCCAAGTTGACCAG

TGCCGTTCCGGTGCTCACCGCGCGCGACGTCGCCGGAGCGGTCGAGTTCT

GGACCGACCGGCTCGGGTTCTCCCGGGACTTCGTGGAGGACGACTTCGCC

GGTGTGGTCCGGGACGACGTGACCCTGTTCATCAGCGCGGTCCAGGACCA

GGTGGTGCCGGACAACACCCTGGCCTGGGTGTGGGTGCGCGGCCTGGACG

AGCTGTACGCCGAGTGGTCGGAGGTCGTGTCCACGAACTTCCGGGACGCC

TCCGGGCCGGCCATGACCGAGATCGGCGAGCAGCCGTGGGGGCGGGAGTT

CGCCCTGCGCGACCCGGCCGGCAACTGCGTGCACTTCGTGGCCGAGGAGC

AGGACTGAATAACTTCGTATAGCATACATTATACGAAGTTATGGCCGCCT

AGGCC-3'.
```

Bacterial Conjugation

To enable transfer of the pglB and acrA transposon cargo into the chromosome of a recipient *E. coli* strain the plasmids pJAN25, pFEB11 or pEFNOV19 were transferred into the *E. coli* strain19851pir$^+$ or direct mating. When necessary the donor *E. coli* strain used was

*E. coli* MFD a diaminopimelic acid (DAP) auxotroph. Growth medium was supplemented with kanamycin 50 μg/ml and ampicillin 100 μg/ml for pJAN25 or pFEB11 whilst chloramphenicol 30 μg/ml and ampicillin 100 μg/ml were added to maintain pEFNOV19. Both donor and recipient bacteria were growth until late exponential phase. Bacterial cells were pelleted by centrifugation, washed 3 times with PBS and mixed together in a ratio of 1:3 recipient to donor and spotted on a dry LB agar plate with no antibiotics for 4-8 hrs. The cells were scraped and suspended in PBS and dilutions plated on LB agar with appropriate selection antibiotics to select for transconjugants. Individual colonies were picked up and screened for loss of the pUT backbone and for the presence of the transposon.

Generation of Unmarked pglB Insertion

The transposon carrying pglB and loxP recombination sites around a Zeocin® resistance cassette was introduced into *E. coli*. Following selection for Zeocin® resistant colonies, the antibiotic selection marker was removed by introduction via electroporation, the temperature sensitive vector pCRE5 (Reference: Appl Environ Microbiol. 2008 February; 74(4): 1064-1075. Genetic Tools for Select- Agent-Compliant Manipulation of *Burkholderia pseudomallei*. Kyoung-Hee Choi, Takehiko Mima, Yveth Casart, Drew Rholl, Ayush Kumar, I for R. Beacham and Herbert P. Schweizer).

*E. coli* was cultured at 28° C. in the presence of kanamycin 50 μg/ml, rhamnose was added to induce expression at 0.2% final concentration and the organism subcultured several times to select for colonies that had lost resistance to Zeocin® but maintained resistance to kanmaycin indicating that the bleomycin resistance gene had been flipped out of the chromosome.

This *E. coli* mutant was then sub-cultured at 42° C. to cure out the pCRE5 plasmid. Screening for colonies that had once again become sensitive to kanamycin confirmed loss of pCRE5 and completed generation of an unmarked inducible copy of pglB on the chromosome of *E. coli.*

To test glycosylation, this *E. coli* strain was transformed with the plasmid pACYCpglB::kan (Linton Molecular Microbiology (2005) 55(6), 1695-1703 Functional analysis of the *Campylobacter jejuni* N-linked protein glycosylation pathway. Dennis Linton, Nick Dorrell, Paul G. Hitchen, Saba Amber, Andrey V. Karlyshev, Howard R. Morris, Anne Dell, Miguel A. Valvano, Markus Aebi and Brendan W. Wren) and the plasmid pWA2 coding for the HIS tagged acceptor protein AcrA (PNAS vol. 102, pp 3016-3021. Engineering N-linked protein glycosylation with diverse O antigen lipopolysaccharide structures in *Escherichia coli.* Mario F. Feldman, Michael Wacker, Marcela Hernandez, Paul G. Hitchen, Cristina L. Marolda, Michael Kowarik, Howard R. Morris, Anne Dell, Miguel A. Valvano, and Markus Aebi).

10 ml of LB broth carrying 30 μg/ml of chloramphenicol and 100 μg/ml of ampicillin to select for pACYCpglB::kan were inoculated with a single colony of *E. coli* strain W3110pglB.

Cultures were incubated at 37° C. with shaking until an optical density 600 nm of 0.6 was reached. IPTG was added to a final concentration of 1 mM and the cultures were incubated for a further 16 hours overnight. Protein was HIS purified and western blots carried out using anti campy glycan and anti HIS antibodies and the images visualised on an Odyssey LI-COR® scanner.

EXAMPLE 1

Figure 6:
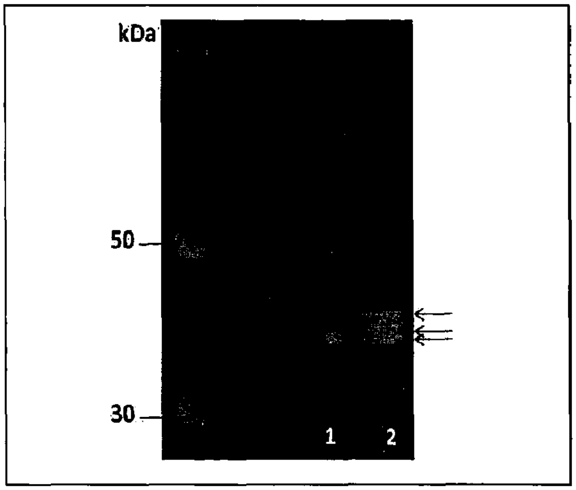
FIG. 6 Glycosylation of AcrA with *S. pneumoniae* capsular polysaccharide. Anti-HIS western blot. Lane 1, AcrA only control; 2 *E. coli* W3110 carrying AcrA and PglB on the chromosome due to an insertion of pEFNOV19: Coding for an IPTG inducible copy of CjPglB and constitutively expressed AcrA from a Tetracycline resistance cassette promoter on a pUTminiTn5km2 backbone. Arrows indicate shift in the size of AcrA only when all the glycosylating components are together.

The *E. coli* strain W3110 carrying a plasmid coding for a *Streptococcus pneumonia* capsular polysaccharide encoded on the plasmid pB4-4 was subjected to conjugation with *E. coli* 19851 pir+ carrying the plasmid pFEB19 coding for an IPTG inducible copy of pglB and a constitutively expressed copy acrA. Previous attempts to make a glycoconjugate using the standard three plasmid system failed presumably due to the combined toxicity of PglB and the metabolic burden of the polysaccharide coding region. The transposon system resulted for the first time in a stable strain. IPTG was added to induce chromosomal expression of pglB and HIS tagged AcrA was purified from the cells using NiNTA binding. FIG. 6 demonstrates how AcrA is shifted in size due to the addition of glycan to the acceptor protein (lane 2). This shift in size does not occur when the glycan is not present (lane 1).

EXAMPLE 2

We have used the transposon pJAN25 carrying an IPTG inducible copy of CjpglB to integrate this gene into the chromosomes of glycoengineering *E. coli* strains W3110, CLM24, CLM37, 5e874, SCM7, SCM6, SCM3.

EXAMPLE 3

We have used the transposon pJAN25 carrying an IPTG inducible copy of CjpglB to integrate this gene into the chromosomes of the following organisms: *Vibrio cholerae, Yersinia pseudotuberculosis, Citrobacter freundii, Actinobacillus pleuropneumoniae.* In the case of *Vibro cholerae* and *Actinobacillus pleuropneumoniae* the standard glycoengineering plasmids used in the tri-plasmid system could not be normally maintained in these organisms.

Figure 7:
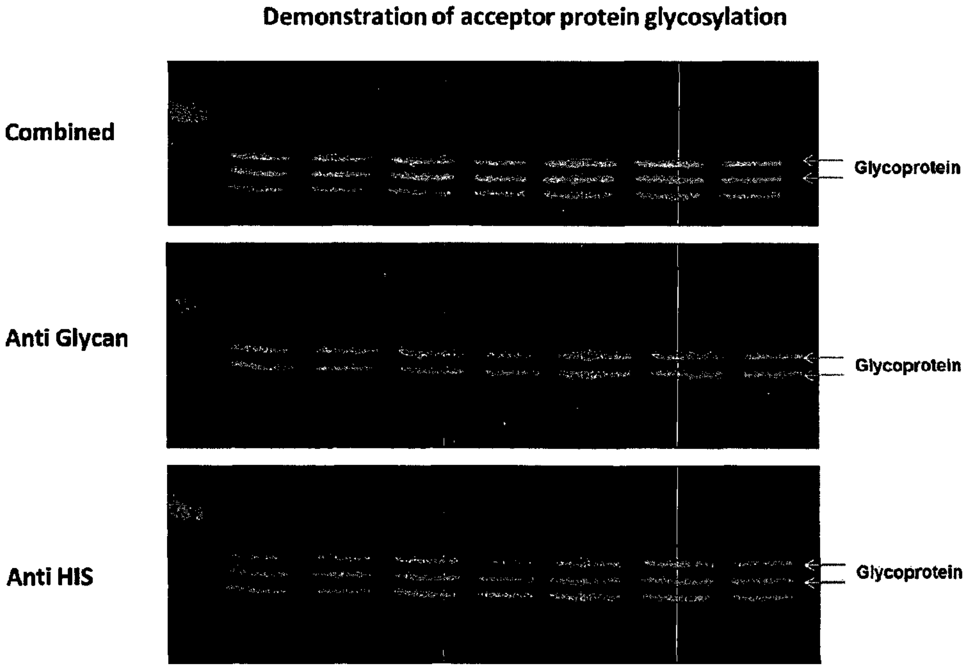
FIG. 7 Demonstration of acceptor protein glycosylation. Western blot using anti-glycan (B), anti-His (C) and both antibodies combined (A). AcrA glycosylated with *C. jejuni* heptasaccharide within *E. coli* W3110 cells carrying unmarked pglB insertion.

EXAMPLE 4 pJCUSA1 has been used to generate a transposon with an IPTG inducible copy of CjpglB and a Zeocin® resistance cassette flanked by loxP recombination sites. This was delivered into a recipient *E. coli* strain by conjugation. This strain can be cured of Zeocin® resistance by the introduction of a CRE recombinase coding plasmid that has a temperature sensitive origin of replication leading to an unmarked *E. coli* strain capable of generating a glycoconjugate. This is illustrated in FIG. 7. The method is used to generate an unmarked chromosomal insertion of the oligosaccharyltransferase coding gene pglB which is exemplified by glycosylation of an acceptor protein.

EXAMPLE 5

Demonstration of the integration of *Campylobacter jejuni* PglB into the chromosome of *Actinobacillus pleuropneumoniae* serotype 8.

*E. coli* Mu free donor cells (MFD) were transformed with the plasmid pJAN25: Coding for an IPTG inducible copy of CjPglB carried on a pUTminiTn5km2 transposon backbone. This donor strain was conjugated with *Actinobacillus pleuropneumoniae* serotype 8 and colonies screened for gain of resistance to kanamycin and no resistance to ampicillin indicating that the transposon had left the backbone and inserted into the chromosome of *A. pleuropneumoniae.*

To demonstrate that this chromosomally inserted copy of pglB was active, membranes were isolated from the newly constructed mutant of *A. pleuropneumoniae* after expression of pglB was induced. 16 h *A. pleuropneumoniae* cultures were diluted 1:25 in fresh media and grown to an OD600 of 0.4-0.6. Expression was induced at this point by addition of IPTG to 1 mM. Incubation was resumed for a further 16 h. Cells were harvested by centrifugation.

Solubilized membranes were prepared by isolating cells expressing CjPglB and by re-suspending the bacterial cell pellet in 2 ml 50 mM Tris-HCl (pH 7.0), 25 mM NaCl and then lysing the pellet using a GE50 ultrasonic processor. Lysates were centrifuged twice at 40 000×g, 4° C. for 20 min to remove unbroken cells. The supernatant was ultracentrifuged at 100 000×g, 4° C. for 1 h, and the resulting total membrane pellet resuspended in 2 ml 50 mM Tris-HCl (pH 7.0), 25 mM NaCl, 1% Triton X-100 per gram of initial wet cell pellet. Samples were incubated at room temperature for 1 h then ultracentrifuged once more at 100 000×g, 4° C. for 1 hour. Supernatants were collected as Triton X-100-solubilised membrane fractions.

The in vitro assay was performed by preparing reaction mixtures that typically contained 3 μl of the fluorescently-labelled peptide FAM-ADQNATA-NH2 (30 μM), 1 μl MnCl2 (150 mM), 4 μl membranes from *A. pleuropneumoniae* expressing CjPglB and 22 μl membrane preparation from *E. coli* expressing the *C. jejuni* heptasaccharide. Samples were incubated at 30° C. with agitation for 16 h. Reactions were stopped by the addition of 10 μl 4×SDS-PAGE gel loading buffer and incubated at 95° C. for 5 min. Samples were loaded on a 4-16% Tricine gel and separated by SDS-PAGE at 30 V for 30 min followed by 200 V for 60 min. Fluorescent peptides were visualized using a Typhoon Trio Imager (FIG. 8).

The invention claimed is:

1. An isolated nucleic acid molecule comprising:

a transcription cassette adapted for expression in a bacterial host cell, said cassette comprising:

a nucleotide sequence encoding an oligosaccharyltransferase enzyme comprising the nucleotide sequence set forth in SEQ ID NO: 22 and a nucleotide sequence encoding an acceptor polypeptide for an oligosaccharide or monosaccharide, wherein the acceptor polypeptide includes an amino acid sequence motif which is a substrate for the oligosaccharyltransferase enzyme.

2. The isolated nucleic acid molecule according to claim 1 where the transcription cassette further comprises a regulatable promoter functionally linked to at least the nucleotide sequence encoding said oligosaccharyltransferase enzyme.

3. The isolated nucleic acid molecule of claim 2, wherein said promoter comprises an inducible nucleotide element conferring regulatable expression in response to an inducer.

4. The isolated nucleic acid molecule of claim 2, wherein said promoter comprises a repressible nucleotide element conferring regulatable expression in response to a repressor.

5. The isolated nucleic acid molecule of claim 1, wherein said nucleotide sequence encoding the oligosaccharyltransferase enzyme consists of:

the nucleotide sequence set forth in SEQ ID NO: 22.

6. The isolated nucleic acid molecule of claim 1, wherein said acceptor polypeptide includes the amino acid motif: Asn-X-Ser or Asn-X-Thr, wherein X is any amino acid except proline.

7. The isolated nucleic acid molecule according to claim 5 wherein said acceptor polypeptide includes the amino acid motif: D/E-X-N-X-S/T, wherein X is any amino acid except proline.

8. The isolated nucleic acid molecule according to claim 7 wherein said acceptor polypeptide including the amino acid motif D/E-X-N-X-S/T, wherein X is any amino acid except proline is selected from the group consisting of: DVNVT (SEQ ID NO: 24), EVNAT (SEQ ID NO: 25), DQNAT (SEQ ID NO: 26), DNNNT (SEQ ID NO: 27), DNNNS (SEQ ID NO: 28), DQNRT (SEQ ID NO: 29), ENNFT (SEQ ID NO: 30), DSNST (SEQ ID NO: 31), DQNIS (SEQ ID NO: 32), DQNVS (SEQ ID NO: 33), DNNVS (SEQ ID NO: 34), DYNVS (SEQ ID NO: 35), DFNVS (SEQ ID NO: 36), DFNAS (SEQ ID NO: 37), DFNSS (SEQ ID NO: 38), DVNAT (SEQ ID NO: 39), DFNVT (SEQ ID NO: 40) and DVNAS (SEQ ID NO: 41).

9. The isolated nucleic acid molecule of claim 1, wherein said transcription cassette comprises a nucleotide sequence that encodes one or more polysaccharide biosynthetic genes.

10. The isolated nucleic acid molecule according to claim 9 wherein said one or more polysaccharide biosynthetic genes are capsular polysaccharides or O antigens.

11. The isolated nucleic acid molecule claim 1, wherein said transcription cassette is adapted by the provision of one or more inverted repeat nucleotide sequences that are transposase recognition sequences.

12. The isolated nucleic acid molecule according to claim 11 wherein said recognition sequence comprises or consists essentially of the nucleotide sequence 5'-CTGTCTCTTGATCAGATCT-3' (SEQ ID NO:7) at the I end and 5'-ACTTGTGTATAAGAGTCAG-3' (SEQ ID NO: 8) at the O end of a miniTn5 transposon.

13. The isolated nucleic acid molecule according to claim 1, wherein said transcription cassette further comprises a nucleotide sequence encoding a bacterial resistance marker gene.

14. The isolated nucleic acid molecule according to claim 13 wherein said bacterial resistance gene confers resistance to an antibiotic.

15. The isolated nucleic acid molecule of claim 13, wherein said bacterial resistance marker gene is adapted by the provision of 5' and 3' flanking nucleotide sequences that include recombination sites.

16. The isolated nucleic acid molecule according to claim 15, wherein said recombination sites comprise or consist essentially of:

```
5' end loxP sequence:
                                        (SEQ ID NO: 9)
5'-ATAACTTCGTATAATGTAT GCTATACGAA GTAG-3'
and

3' end loxP sequence:
                                       (SEQ ID NO: 10)
5'-ATAAC TTCGTATAATGTATGCTATA CGAAGTTAT-3';
or

                                       (SEQ ID NO: 11)
5'-GAAGT TCCTATTCCG AAGTTCCTAT

TCTCTAGAAAGTATAGGAAC TTC-3'
and

                                       (SEQ ID NO: 12)
5'-GAAGTACCTATTC CGAAGTTCCT ATTCTCTAGA

AAGTATAGGA ACTTC-3'.
```

17. A vector comprising the nucleic acid molecule of claim 1.

18. The vector according to claim 17 wherein said vector is a plasmid or a transposon.

19. A bacterial cell genetically modified with the nucleic acid molecule of claim 1.

20. A bacterial cell culture comprising the genetically modified bacterial cell of claim 19.

21. A process for the production of one or more glycoconjugates comprising:

i) providing a bacterial cell culture according to claim 20;

ii) providing cell culture conditions; and iii) isolating one or more glycoconjugates from the bacterial cell or cell culture medium.

22. A cell culture vessel comprising a bacterial cell culture according to claim 20.

23. A method for the stable integration of a transposable element into a bacterial genome comprising:

i) forming a cell culture preparation comprising a bacterial cell and the transposon of claim 18;

ii) incubating the preparation to allow stable integration of the transposon;

iii) selecting bacterial cells that have stably integrated the transposon using culture conditions that select for bacterial cells that are stable integrants; and iv) cloning bacterial cells that have stably integrated the transposon.

24. The method according to claim 23, wherein the cloned bacterial cells are contacted with a vector comprising a nucleotide sequence that encodes a recombinase that deletes all or part of said bacterial resistance marker gene.

25. The method according to claim 24, wherein said recombinase is specific for recombination sites comprising or consisting essentially of the nucleotide sequence:

```
5' end loxP sequence:
                                        (SEQ ID NO: 9)
5'-ATAACTTCGTATAATGTAT GCTATACGAA GTAG-3',
and

3' end loxP sequence:
                                       (SEQ ID NO: 10)
5'-ATAAC TTCGTATAATGTATGCTATA CGAAGTTAT-3';
or

                                       (SEQ ID NO: 11)
5'-GAAGT TCCTATTCCG AAGTTCCTAT

TCTCTAGAAAGTATAGGAAC TTC-3';
and

                                       (SEQ ID NO: 12)
5'-GAAGTACCTATTC CGAAGTTCCT ATTCTCTAGA

AAGTATAGGA ACTTC-3'.
```

26. A process for the identification of novel glycoconjugates comprising:

i) forming a cell culture preparation comprising a bacterial cell and the transposon of claim 18;

ii) incubating the preparation to allow stable integration of the transposon;

iii) selecting bacterial cells that have stably integrated the transposon using culture conditions that select for bacterial cells that are stable integrants;

iv) cloning bacterial cells that have stably integrated the transposon;

v) isolating glycoconjugates from the cloned bacterial cells or cell culture medium; and vi) analysing the monosaccharide or polysaccharide content of said isolated glycoconjugate.

27. A method for the delivery of a transposable element to a bacterial cell comprising:

i) providing a vector adapted for high copy number replication in a bacterial cell comprising: the nucleic acid molecule of claim 1, a nucleotide sequence encoding an antibiotic resistance gene cassette wherein the antibiotic resistance gene cassette is flanked by recombination sequences recognized by a recombinase and wherein the cassettes are flanked by restriction sites for excision and delivery into a transposon delivery vector;

ii) providing a transposon delivery vector comprising restriction sites flanked by inverted repeats for delivery of a transposable element to a bacterial cell;

iii) sub-cloning the vector in (i) into the delivery vector in (ii) to provide a modified delivery vector;

iv) transferring the modified delivery vector in (iii) to a bacterial cell and selecting stably integrated bacterial cells by antibiotic resistance;

v) cloning stably integrated bacterial cells; and optionally vi) transforming the stably integrated bacterial cells with a vector comprising a nucleotide sequence encoding a recombinase that excises the antibiotic resistance genes from the genome of the stably integrated bacterial cells.

* * * * *